United States Patent
Jenkins et al.

(10) Patent No.: US 6,831,273 B2
(45) Date of Patent: Dec. 14, 2004

(54) ION MOBILITY SPECTROMETERS WITH IMPROVED RESOLUTION

(75) Inventors: Anthony Jenkins, North Reading, MA (US); William J. McGann, Raynham, MA (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 10/628,753

(22) Filed: Jul. 28, 2003

(65) Prior Publication Data

US 2004/0056191 A1 Mar. 25, 2004

Related U.S. Application Data

(60) Provisional application No. 60/400,192, filed on Jul. 31, 2002.

(51) Int. Cl.[7] .................................................. H01J 49/40
(52) U.S. Cl. ....................................... 250/287; 250/282
(58) Field of Search .................................. 250/287, 282

(56) References Cited

U.S. PATENT DOCUMENTS

| | | |
|---|---|---|
| 3,596,088 A | 7/1971 | Cohen |
| 3,699,333 A | 10/1972 | Cohen et al. |
| 4,390,784 A | 6/1983 | Browning et al. |
| 4,772,794 A | 9/1988 | Jenkins |
| 4,818,869 A | 4/1989 | Weber-Grabau |
| 4,855,595 A | 8/1989 | Blanchard |
| 5,027,643 A | 7/1991 | Jenkins |
| 5,200,614 A | 4/1993 | Jenkins |
| 5,291,017 A | 3/1994 | Wang et al. |
| 5,420,424 A | 5/1995 | Carnahan et al. |
| 5,491,337 A | 2/1996 | Jenkins et al. |
| 6,073,499 A | 6/2000 | Settles |
| 6,121,607 A | 9/2000 | Whitehouse et al. |
| 6,124,592 A | 9/2000 | Spangler |
| 6,193,866 B1 | 2/2001 | Bader et al. |
| 6,410,914 B1 | 6/2002 | Park et al. |
| 6,630,662 B1 | 10/2003 | Loboda |
| 2002/0134932 A1 | 9/2002 | Guevremont et al. |
| 2002/0134933 A1 | 9/2002 | Jenkins et al. |
| 2003/0213903 A1 * | 11/2003 | Ichimura et al. ............ 250/282 |

FOREIGN PATENT DOCUMENTS

| | | |
|---|---|---|
| EP | 0 253 155 | 1/1988 |
| GB | 1 248 414 | 10/1971 |

* cited by examiner

*Primary Examiner*—Jack I. Berman
(74) *Attorney, Agent, or Firm*—Gerald E. Hespos; Anthony J. Casella

(57) ABSTRACT

An apparatus is provided for detecting whether substances of interest are present in a sample of air. The apparatus includes a detector, such as an ion trap mobility spectrometer. The detector is operated at a high drift voltage and then is switched to a low drift voltage. Spectra are collected at the high and low field strengths and are compared with standard spectra at those strengths to determine whether materials of interest are present.

15 Claims, 1 Drawing Sheet

ION MOBILITY SPECTROMETERS WITH IMPROVED RESOLUTION

This application claims priority on U.S. Provisional Patent Appl. No. 60/400,192, filed Jul. 31, 2002.

BACKGROUND OF THE INVENTION

1. Field of the Invention

The invention relates to ion mobility spectrometers that can be used to detect the presences of minuet amounts of substances of interest.

2. Description of the Related Art

Previous ion mobility spectrometers and ion trap mobility spectrometers are capable of uniquely identifying approximately 100 peaks in the drift spectrum. For many applications in drug and explosive trace detection this provides sufficient resolution to identify the target materials while maintaining very low false positive responses. This performance level is largely achieved by the use of dopants to eliminate many unwanted ionic species from innocent materials, thus producing simpler spectra with fewer "peaks". An example of an effective use of dopants is disclosed in U.S. Pat. No. 5,491,337.

More recent improvements have been developed in which both positive and negative ion spectra are produced from the same sample. Such improvements are disclosed in U.S. patent application Ser. No. 10/103,601. This allows improved resolution for materials that produce both negative and positive ion spectra. It also allows both drugs and explosives to be detected in the same sample.

Yet another improvement allows the reaction rate chemistry of the ion transfer reactions to be measured prior to drifting ions down the drift tube, as disclosed in U.S. patent application Ser. No. 09/910,197. This provides increased detection capability and resolution by recording the ionic spectrum or plasmagram at selected time intervals after injecting charge into the reaction chamber of the spectrometer.

The above methods and improvements have allowed superb detection and identification of most drugs and explosives. However, some ionic species remain difficult to identify separately.

The dopants added to the carrier flow entering the detector scavenge the charge from the weaker charge affinity materials. Thus, there is also a need to detect and identify a wide range of materials that would not normally be ionized.

The present invention provides for further increases in resolution (ability to determine the difference between two similar ions) and an increase in the range of materials that can be identified uniquely.

SUMMARY OF INVENTION

The present invention is a method and apparatus which modifies the design of either an ion mobility spectrometer (IMS) or an ion trap mobility spectrometer (ITMS) to provide improved resolution between coincidental or closely spaced peaks in the mobility spectrum. For example, the peaks from tetrahydro cannabinol (active ingredient in marijuana) and heroin are closely spaced. These two ions normally can be separated with some care to maintain all conditions constant, but occasionally the heroin contains other opiates such as papavarene, which makes the separation extremely difficult.

The time of flight of a specific ion is decided by the length of the drift tube, the electric field strength down the drift tube, and the mass and shape of the ion. The shape factor is difficult to predict, but generally, a more spherical ion will normally take a shorter time than an ion of the same mass which is more elongate. As the field strength is increased, ions which exhibit a dipole moment may have more tendency to align with the field. This means that they may "tumble" less in a high field than in a low field. Thus the shape and polarity factor may cause two ions which have identical drift times at one field strength to have differing drift times at a different field strength. This parameter has been used in asymmetric field effect ion mobility detectors to provide a detection capability. The performance of such detectors has been inferior to traditional ion mobility detectors because only one ionic species can be measured at one time, and scanning through the range of differential mobilities is relatively slow.

The present invention takes advantage of the performance of the IMS and ITMS with the additional advantage of the asymmetric field effect ion mobility spectrometer. After a substance is detected and tentatively identified, the field strength is reduced electrically by reducing the voltage supplied to the field defining electrodes in the drift tube. This reduces the mobility of all ions, but not all are changed in proportion to the original drift time at high field strength. The peak shift between the two ion spectra is measured and compared against standard shifts held in a library or storage to confirm the identity of the material. If no match is obtained then the substance is unknown and is not identified. Thus false alarms from unknown materials are eliminated.

DETAILED DESCRIPTION OF THE PREFERRED EMBODIMENT

Figure 1:
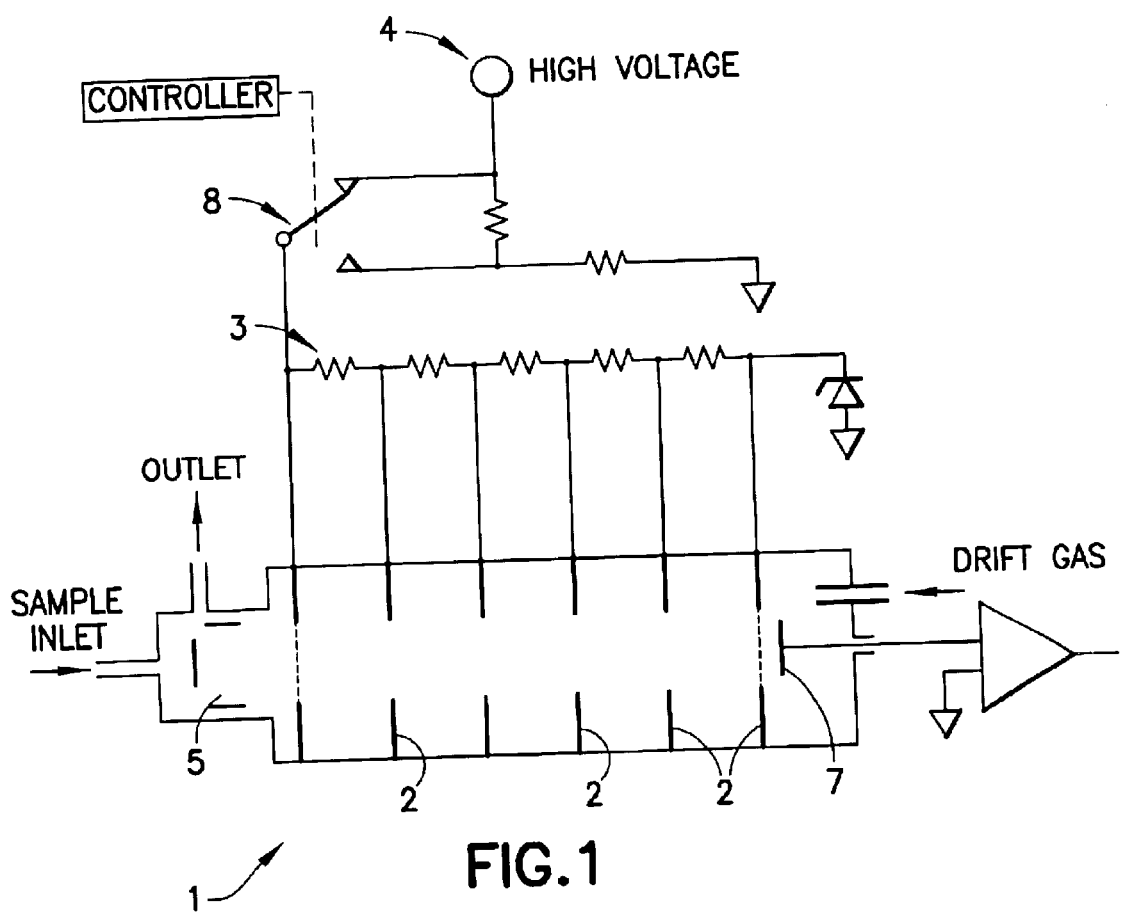
FIG. 1 is a schematic illustration of a high field/low field circuit applied to an ion mobility spectrometer in accordance with the invention.

One embodiment of the design is shown in FIG. 1. The ion mobility detector 1 can be any of previously known detectors, IMS or ITMS. Furthermore, the design works with switchable, positive and negative detection systems as described in U.S. patent application Ser. No. 10/103,601. Also, the design is suitable for operation with the high frequency plasma discharge detector described in U.S. patent application Ser. No. 09/910,197. The field defining electrodes 2 which produce a continuous electric field down the drift tube are connected to a ladder network of resistors 3, which in turn are connected to a source of high voltage 4. The high voltage source 4 is held typically between 1000 and 1500 volts. The sample is introduced into the reaction chamber 5, of the detector, where molecules of interest are ionized. The ions are expelled down the drift tube at intervals of approximately 20 mS, where they move under the influence of the high field and are collected at the collector electrode 7. In an existing design, most of the ions of interest arrive at the collector electrode within 10 mS. In the present embodiment, the high field may be switched alternately by operation of the switch 8 to provide a low field strength down the drift tube. The low filed strength preferably is half or less than half of the high field strength. Spectra are collected alternately at high and low field strengths and are compared with standard spectra from a library or storage to determine whether materials of interest are present.

In another embodiment of the design, the detector is operated at high field strength continuously. When a substance of interest is detected by the normal means, a confirmatory plasmagram may be obtained by switching to low field. In this way, two orthogonal measurements are made of both ion mobility and ion shape. This in turn leads to greater resolution and lower false alarms.

This new embodiment allows the detector to be operated without dopants added to the carrier flow. Normally, operation without dopant materials would allow many unwanted substances to be analyzed, producing very high false alarm rates. With the added specificity of the ionic "shape" measurement, false alarms can be held at acceptable levels without dopant materials. This is particularly useful to the high frequency plasma discharge ionization technique, since much higher charge densities can be injected into the reaction chamber, which provides a greater probability of ionization for molecules of low charge affinity. With previous embodiments, high charge densities necessitate higher dopant concentrations in order to maintain low false alarm rates.

When coupled with the high frequency plasma ionization and no dopant chemistry, this new method of operation allows many more substances to be detected at very high sensitivity. This provides a capability of detecting a much wider range of materials, such as human body odors, which may be used for diagnosis of diseases. Also, some of the plastic explosives which have very low vapor pressure from the active explosive ingredient can now be detected by the vapor emission from the plasticizer. It is well known that dogs do not detect the active explosive ingredient of plastic explosives, but rely on detection of solvents and vapors from the plasticizers. This new method can, therefore, be employed to detect more threat materials by vapor emissions which are not detected by previous ion mobility detectors.

What is claimed is:

1. An apparatus for detecting whether a substance of interest is present in a sample of air, comprising;
   an inlet for delivering the sample of air;
   an ion mobility detector in communication with the inlet and operable alternately at high and low drift voltage levels for detecting whether the substance of interest is present;
   at least one source of high voltage for applying a high drift voltage to the detector; and
   a controller communicating with the detector and the source of high voltage for selectively reducing the voltage to the detector to a low drift voltage.

2. The apparatus of claim 1, wherein the controller is operative to switch between supplying high drift voltage and low drift voltage for each sample of air delivered by the inlet.

3. The apparatus of claim 1, wherein the controller is operative to switch from the high drift voltage to the low drift voltage only when the detector detects the presence of the substance of interest while operating at the high drift voltage.

4. The apparatus of claim 1, wherein the controller comprises a switch for selectively placing at least one resistor in communication with the detector for reducing the voltage to the low drift voltage.

5. The apparatus of claim 1, wherein the ion mobility detector is an ion trap mobility spectrometer.

6. An apparatus for detecting whether substances of interest are in any of plurality of samples of air, said apparatus comprising;
   an inlet for receiving one of the samples of air;
   a reaction chamber communicating with the inlet and operative for ionizing molecules in the reaction chamber;
   a drift tube in communication with the reaction chamber;
   a collector electrode in the drift tube at a location spaced from the reaction chamber;
   at least one field-defining electrode in the drift tube between the reaction chamber and the collector electrode;
   at least one source of voltage for applying a drift voltage across the field-defining electrode; and
   a controller for selectively switching between a high drift voltage and a low drift voltage for alternating between a high field strength and a low field strength in the drift tube.

7. The apparatus of claim 6, wherein the high drift voltage is between approximately 1,000 volts and 1,500 volts.

8. The apparatus of claim 6, further comprising a processor communicating with the collector electrode, the processor having a storage device for storing data indicative of substances of interest in the high field strength and a comparator for comparing data of ions arriving at the collector electrode when the voltage source is operated at said high drift voltage with known data for the substances of interest.

9. The apparatus of claim 8, wherein the storage device of the processor further stores data indicative of substances of interest in the low field strength, and the comparator further being for comparing data of ions arriving at the collector electrode when the voltage source is operated at said low drift voltage with known data for the substances of interest.

10. The apparatus of claim 9, wherein the controller switches from the high field strength for each of said samples.

11. The apparatus of claim 9, wherein the controller communicates with the processor and switches to the low field strength only when the processor identifies a substance of interest while at the high field strength.

12. A method for testing samples of air to determine whether any of the samples of air contain a substance of interest, the method comprising;
   delivering one of the samples of air to an ion mobility detector;
   operating the detector at a first drift voltage level to test for a presence of the substance of interest in the sample; and
   operating the detector at a second drift voltage level to test for the presence of the substance of interest.

13. The method of claim 12, wherein the second drift voltage level is lower than the first drift voltage level.

14. The method of claim 12, wherein the step of operating the detector at the second drift voltage level is carried out for each sample of air tested by the method.

15. The method of claim 12, wherein the step of operating the detector at the second drift voltage level is carried out only when the step of testing the sample of air at the first drift voltage level identifies a substance of interest.

* * * * *